(12) United States Patent
Farkas et al.

(10) Patent No.: US 6,884,424 B2
(45) Date of Patent: Apr. 26, 2005

(54) METHOD FOR TREATING THE PATHOLOGICAL LESIONS OF THE SKIN THAT DEVELOP BY ULTRAVIOLET RADIATION OF THE SUNLIGHT

(75) Inventors: Bea Farkas, Szeged (HU); Peter Literati Nagy, Budapest (HU); Agnes Vadasz, Budapest (HU); Laszlo Vigh, Szeged (HU)

(73) Assignee: N-Gene Research Laboratories Inc., New York, NY (US)

( * ) Notice: Subject to any disclaimer, the term of this patent is extended or adjusted under 35 U.S.C. 154(b) by 20 days.

(21) Appl. No.: 10/005,074

(22) Filed: Dec. 7, 2001

(65) Prior Publication Data

US 2002/0131938 A1 Sep. 19, 2002

Related U.S. Application Data

(63) Continuation-in-part of application No. 09/205,281, filed on Dec. 4, 1998, now Pat. No. 6,458,371, which is a continuation-in-part of application No. 08/771,410, filed on Dec. 20, 1996, now abandoned.

(30) Foreign Application Priority Data

Dec. 22, 1995 (HU) ............................................. 9503728

(51) Int. Cl.$^7$ ..................... A61K 7/00; A61K 31/155; A61K 31/445; A01N 25/00
(52) U.S. Cl. ..................... 424/401; 514/315; 514/633; 514/844; 514/846
(58) Field of Search ......................... 424/401; 514/315, 514/633, 844, 846

(56) References Cited

U.S. PATENT DOCUMENTS

| | | | |
|---|---|---|---|
| 4,187,220 A | 2/1980 | Takacs et al. ............... | 260/239 |
| 4,308,399 A | 12/1981 | Takacs et al. ............... | 564/257 |
| 5,296,606 A | 3/1994 | Nagy et al. .................. | 546/193 |
| 6,440,998 B1 * | 8/2002 | Sumegi ....................... | 514/318 |
| 6,451,851 B1 * | 9/2002 | Sumegi ....................... | 514/507 |
| 6,458,371 B1 * | 10/2002 | Farkas et al. ............... | 424/401 |
| 6,656,955 B1 * | 12/2003 | Sumegi ....................... | 514/318 |

FOREIGN PATENT DOCUMENTS

| WO | WO98/58675 | * 12/1998 | .......... A61K/45/06 |
|---|---|---|---|
| WO | WO98/58676 | * 12/1998 | .......... A61K/45/06 |

OTHER PUBLICATIONS

Kurihara et al., *Chemical Abstracts Plus*, vol. 94, #30304, 1981.
Takacs et al., *Chemical Abstracts Plus*, vol. 89, #6123, 1978.
Lion, *World Patent Index*, 83–720852, 1983.
Bissett et al., *Chemical Abstracts*, vol. 112, #223133, 1990.

* cited by examiner

*Primary Examiner*—Shengjun Wang
(74) *Attorney, Agent, or Firm*—Birch, Stewart, Kolasch & Birch, LLP

(57) ABSTRACT

The invention relates to methods for prevention and/or treatment of skin lesions caused by exposure to ultraviolet radiation. Exemplary condition that can be prevented or treated are actinic keratosis, dry skin, polymorphic light exanthema, photopathology, photo-allergy, solar atrophy, stria migrans, elastoma diffusum, X-ray dermatitis, gouty polychondritis and decubitis ulcer. The method employs application to the skin of a composition comprising a hydroximic acid derivative of the formula $$R^3-A-\underset{\underset{NH_2}{|}}{C}=N-O-CH_2-\underset{\underset{OH}{|}}{C}H-CH_2-N\underset{R^2}{\overset{R^1}{\diagup}} \quad I$$

7 Claims, No Drawings

METHOD FOR TREATING THE PATHOLOGICAL LESIONS OF THE SKIN THAT DEVELOP BY ULTRAVIOLET RADIATION OF THE SUNLIGHT

This application is a continuation-in-part of application Ser. No. 09/205,281 filed on Dec. 4, 1998 (Pat. No. 6,458,371 issued Oct. 1, 2002), which is a continuation-in-part of application Ser. No. 08/771,440 filed Dec. 20, 1996; priority of both of these applications is claimed under 35 U.S.C. § 120. The entire contents of these applications are hereby incorporated by reference. This application also claims priority of Application No. P9503728 filed in Hungary on Dec. 22, 1995 under 35 U.S.C. § 119; the entire contents of which are hereby incorporated by reference.

FIELD OF THE INVENTION

The invention refers to a method for treating the pathological lesions of the skin that normally develop due to the ultraviolet (UV) radiation of the sunlight.

BACKGROUND OF THE INVENTION

Exposure of human skin to sunlight has several known unpleasant effects such as sunburn and pathological lesions leading to carcinogenesis. Due to the ultraviolet radiation of sunlight, free radicals (e.g. hydroxy radicals or nascent oxygen) form in the skin. Such free radicals can injure the DNA of skin cells and contribute to photoaging of the skin.

Photoaging is characterized by clinical, histological and biochemical changes which differ from alterations in chronologically aged but sunprotected skin [Herschenfeld, R. E. et al.: The cumulative effect of ultraviolet radiation on the skin photoaging, in *Photodermatology*, Hawk, J. L. M., Ed., Arnold, London, Sydney, Oakland, 1999, 89–102]. Photoaging includes changes attributable to chronic sun exposure and results in dry skin, wrinkling, laxity or even a variety of benign neoplasms.

Free radicals having a powerful oxidizing effect can injure the membrane of cells by oxidizing the unsaturated fatty acid components of the membrane (peroxidization of lipids). Also, reactive aldehydes are formed during the oxidization. In the injury of the membrane, increased intake of calcium leads to cell death, and pathological processes are started due to the presence of the reactive aldehydes:

injury of DNA, resulting in mutation in both the cell nucleus and mitochondria;

changes in the properties of the interstitial proteins (i.e. elastin) owing to the formation of crosslinks.

It is known that the elastic structures of collagen proteins and elastin contain a lot of water. It is characteristic of the interstitial proteins that they are rich in lysine. The reactive aldehydes such as malondialdehyde result in condensation reactions with the protein side chains containing amino groups to yield crosslinks. Thus, the originally elastic structure of the skin becomes rigid and hydrophobic. During the above process, at first lipofuscin ceroids, then age pigments are formed.

The natural protective mechanism against UV radiation include bronzing due to the formation of melanin, DNA repair mechanisms, etc. Deficiency of a protective mechanism such as DNA repair, with consequent loss of the correction of the DNA injuries caused by UV radiation leads to early photoaging of the skin. Xeroderma pigmentosum is a disease characterized by deficiency of DNA repair that can be accompanied by the development of a malignant tumor. Sunburn spots caused by bronzing in early childhood are photodamage that heals, leaving an extended scar that can result in spinocellular carcinoma or even in various malignant tumors (e.g. melanoma, cerato-acanthoma, basalioma, sarcoma).

Thus, UV radiation-induced injury to the skin can be subdivided into acute photodamage (e.g. sunburn) and chronic photodamage (e.g. photoaging, actinic keratosis, and, ultimately, skin cancers).

Actinic keratosis is a common sun-induced precancerous neoplasm confined to the epidermis. It is the initial manifestation of a continuum of clinical and histologic abnormalities that progresses to invasive squamous cell carcinoma, a disorder that accounts for thousands of death in the USA each year. [Schwartz, R. A.: The Actinic Keratosis, Dermatol. Surg., 23, 1009–1019 (1997).]

Actinic keratosis has been known by a variety of names, including solar keratosis, senile keratosis, senile hyperkeratosis, keratoma senile, and keratosis senilis. The actinic keratosis is a skin-colored to reddish brown or yellowish black ill-defined round or irregularly shaped macule or papule with a dry firmly adherent scale. It is usually 1–3 mm in diameter, but varies up to several centimeters, and can be seen on sun-exposed body regions in persons with many years of solar exposure.

Since the actinic keratosis is the most common precancerous skin lesion, there is an existing demand for a method that is efficient in the treatment of the pathological lesions of the skin to avoid the formation of more severe forms e.g. actinic keratosis. As a matter of fact, with the excepton of new-born babies, parts of the skin surface of nearly everybody have been exposed to the UV radiation of sunlight for a shorter or longer time, consequently, some sorts of pathological lesions of the skin develop when a higher age is reached.

The hydroximic acid derivatives of Formula I below are known from Hungarian Patent No. 177 578 and its equivalent U.S. Pat. No. 4,308,399. The known compounds are suitable for the treatment of diabetic angiopathy.

DESCRIPTION OF THE INVENTION

The invention refers to a method for treating the pathological lesions of the skin that develops by UV radiation of the sunlight comprising applying to the affected skin surface an effective amount of a hydroximic acid derivative of Formula

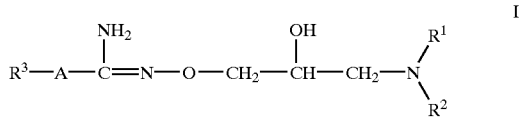

wherein $R^1$ is a hydrogen atom or a $C_{1-5}$ alkyl group;

$R^2$ is a hydrogen atom or a $C_{1-5}$ alkyl group, a $C_{5-7}$ cycloalkyl group or a phenyl group optionally substituted by a hydroxy group; or $R^1$ and $R^2$ together with the nitrogen atom to which they are attached form a 5- to 8-membered ring that optionally comprises one or more further nitrogen or oxygen atoms, wherein said ring can be optionally condensed with a benzene ring;

$R^3$ is a hydrogen atom, a phenyl group, a naphthyl group or a pyridyl group wherein said groups can optionally be substituted by one or more halo atoms or $C_{1-4}$ alkoxy groups;

A is a group of Formula

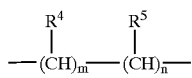

wherein
$R^4$ is a hydrogen atom or a phenyl group;
$R^5$ is a hydrogen atom or a phenyl group;
m has a value of 0, 1 or 2; and
n has a value of 0, 1 or 2;
or a physiologically acceptable acid addition salt thereof in form of a composition suitable for local treatment.

The aim of the invention is to provide a method for the prevention or reduction of the pathological lesions of the skin.

It was found that the above aim is fulfilled by the method of the invention according to which the skin surface affected by the UV radiation of the sunlight is treated with a composition suitable for local treatment and containing an effective amount of a hydroximic acid derivative of Formula I or a physiologically acceptable acid addition salt thereof.

"Treating the pathological lesions of the skin" means both preventing the formation of the pathological lesions of the skin and reducing the pathological lesions of the skin. Thus, when the skin is treated with a composition suitable for local treatment and containing an effective amount of a hydroximic acid derivative of Formula I or a physiologically acceptable acid addition salt thereof before each exposure to UV radiation of the sunlight—practically no further photodamage is experienced while the skin is repeatedly exposed to UV light radiation of the usual intensity during outdoor activities or outdoor staying for a longer time i.e. years or decades.

In case of a human being practically without any signs of pathological lesion, the formation of such lesion can be prevented by the method of the invention. In case of a human being with accumulated expositions to the UV radiation of the sunlight in the past and, thus, with some degree of pathological lesion of the skin, no deterioration is experienced on further exposition to the UV radiation when the exposed skin surface is regularly treated according to the method of the invention. For example, in case of a farmer who have spent decades in outdoor work, macules of actinic keratosis may appear on the neck or forearm exposed to the UV radiation of the sun. Once these macules are removed surgically to avoid the formation of carcinoma, and the exposed skin surface is regularly treated with a composition suitable for local treatment and containing an effective amount of a hydroximic acid derivative of the formula I or a physiologically acceptable acid addition salt thereof, further macules of actinic keratosis do not develop, although, the farmer continues his earlier activities.

The pathological lesions of the skin include especially the followings:
dry skin;
actinic keratosis, purpura senilis;
polymorphic light exanthema;
toxic photopathy;
photo-allergy;
solar atrophy of skin;
puberal strias (stria migrans);
elastoma diffusum (old skin);
X-ray dermatitis;
gouty polychondritis;
decubitus (bedsore).

The term "composition" as used herein means a formulation that is suitable for local or topical treatment and which is applied to the skin surface in a conventional manner.

The composition employed according to the method of the invention comprises a hydroximic acid derivative of Formula I or a physiologically acceptable acid addition salt thereof as the active ingredient in admixture with one or more conventional carrier(s) of topical compositions that are suitable for the treatment of the skin surface.

A $C_{1-5}$ alkyl group is, for example, a methyl, ethyl, n-propyl, isopropyl, n-butyl or n-pentyl group, preferably a methyl or an ethyl group.

A $C_{5-7}$ cycloalkyl group is a cyclopentyl, cyclohexyl or cycloheptyl group, preferably a cyclopentyl or cyclohexyl group.

A 5- to 8-membered ring containing a nitrogen atom and optionally one or more further nitrogen or oxygen atoms can be, for example, a pyrrole, pyrazole, imidazole, oxazole, thiazole, pyridine, pyridazine, pyrimidine, piperidine, piperazine, morpholine, indole or quinoline ring.

A halo atom is, for example, a fluoro, chloro, bromo or iodo atom, preferably a chloro or bromo atom.

A $C_{1-4}$ alkoxy group is, for example, a methoxy, ethoxy, isopropoxy, n-propoxy or n-butoxy group, preferably a methoxy or ethoxy group.

The physiologically acceptable acid addition salts of the compounds of Formula I are the acid addition salts formed with physiologically acceptable inorganic acids such as hydrochloric acid, sulfuric acid, etc. or with physiologically acceptable organic acids such as acetic acid, fumaric acid, lactic acid, etc.

A preferred subgroup of the compounds of Formula I consists of the hydroximic acid derivatives of Formula I wherein $R^1$ and $R^2$ together with the nitrogen atom to which they are attached form a piperidino group, $R^3$ is a pyridyl or a phenyl group and A represents a group of the formula a, wherein m and n have a value of 0. An especially preferred compound is the following: O-(3-piperidino-2-hydroxy-1-propyl)nicotinic amidoxime (Compound "A").

The compounds of Formula I can be prepared by the processes known from U.S. Pat. No. 4,308,399.

The composition suitable for local or topical treatment of the skin surface contains, in general, 0.1 to 30% by mass, preferably 5 to 15% by mass of a hydroximic acid derivative of the formula I or a physiologically acceptable acid addition salt thereof as the active ingredient and conventional carriers used in topical formulations. The composition used according to the method of the invention includes mainly creams and liniments based on water/oil or oil/water emulsions.

The conventional carriers used in topical formulations are basically the same ones employed in cosmetic formulations, for example, one- or two-basic alcohols having a saturated or an unsaturated carbon chain such as cetyl alcohol, stearyl alcohol, cetylstearyl alcohol, oleyl alcohol, lauryl alcohol, ethylene glycol, propylene glycol, glycerol, etc.; natural fats and oils such as olive oil, wheat-germ oil, maize-germ oil, lanolin, cocoa-butter; higher hydrocarbons such as vaseline oil, vaseline; beeswax; cellulose derivatives; emulsifiers such as sodium lauryl sulfate, fatty acid or oleic acid esters of sorbitan, fatty acid or oleic acid esters of poly(ethylene glycol), sorbitan ethers of fatty alcohols or oleic alcohols, poly(ethylene glycol) ethers of fatty alcohols or oleic alcohols, glycerides of fatty acids, etc.; preservatives such as methyl p-hydroxybenzoate, chlorohexidine gluconate, etc.

The composition employed according to the method of the invention is prepared by blending the ingredients thereof in a manner known per se. In general, the ingredients of the fatty phase and those of the aqueous phase are separately admixed, then the two phases are blended using elevated temperature, if required. The active ingredient of Formula I is added, preferably in an aqueous solution, to the fatty phase or to the mixture of the other ingredients.

The effect of the hydroximic acid derivatives of Formula I on the formation of the pathological lesions of the skin was studied in the following test.

Age-matched groups of hairless mice were pretreated with the cream of Example 3 (that contained 15% of O-(3-piperidino-2-hydroxy-1-propyl)nicotinic amidoxime monohydrochloride as the active ingredient) or the vehicle prior to UVB exposure in the uncovered area of skin surface of the back, then the pretreated areas were exposed to UVB radiation in a dose that causes minimal erythema (1 MED) to induce photoaging. A Waldmann UV 8001 K light booth (Waldmann) equipped with UV21 Philips lamps (13 tubes) was used as UVB source. The major peak of these lamps is at 313 nm. The minimal erythema dose (MED) energy of the UVB irradiation (i.e. the energy of UVB irradiation required to produce the minimally perceptible erythema reaction of the skin) was determined on six unprotected skin surface areas (0.25 $cm^2$ each) of animals exposed to increasing doses (0.07 to 0.32 $J/cm^2$ with an increment of 0.05) of UVB. All other body sites were covered. Reading was carried out 24 hours after UV exposure.

The procedures of pretreatment and UVB exposure were repeated five times weekly, and the test lasted for 32 weeks. At the end of each week, the macro- and micromorphological changes of the exposed skin surfaces were detected. The pretreated and exposed animals were compared to the untreated-unexposed control group of animals undergoing chronological aging process without photoaging. Animals were scored for skin lesions and the appearance and number of skin tumors were detected.

The first tumor appeared 18 weeks after starting UV exposure in vehicle-pretreated animals. By week 23, all animals in this group (i.e. 12 animals) had one or more skin tumors of at least 1 mm diameter. At the end of the UV treatment (week 32), all lesions were examined histologically. Histopathological changes in elastic fiber network were recognized by Orcein-Giemsa staining, thickening of the epidermis and carcinogenesis were followed by H&E staining and immunohistological reaction with p53 antibody.

In case of UV-exposed animals pretreated with the composition of Example 3, no pathological changes could be observed except a 1.5–2-fold thickening of the epidermis with hypergranulosis. Thus, it could be established that pretreatment with the tested hydroximic acid derivative protected against the manifestation of an in situ or invasive carcinoma during the 32-week study period.

It is to be noted that in case of mice, the expectation of life amounts to about 2 years i.e. 104 weeks, thus, the 32 weeks' UV exposure period corresponds to about 30% of the length of life of a mouse. In men, this means more than 20 years of UV exposure, consequently, a rather long-lasting UV exposure was simulated.

In summary, from the above test it follows that long-lasting UVB exposures of the skin surface, without suitable protection thereof, produce skin tumor, while the hydroximic acid derivatives of Formula I can prevent the incidence of pathological changes of the skin, consequently, neither precancerous skin lesions, nor skin tumor forms.

The invention is further elucidated by means of the following Examples.

EXAMPLE 1

Cream (Oil/Water)

| The cream consists of the following ingredients: | |
|---|---|
| compound „A" | 5.0% by mass |
| cetylstearyl alcohol | 7.5% by mass |
| stearic acid | 9.0% by mass |
| glycerol monostearate | 2.0% by mass |
| sodium lauryl sulfate | 0.5% by mass |
| methyl p-hydroxybenzoate | 0.1% by mass |
| distilled water | 75.9% by mass |
| | 100.0% by mass |

The lipophilic ingredients (cetylstearyl alcohol, stearic acid and glycerol monostearate) are melted over a water bath. The sodium lauryl sulfate and methyl p-hydroxybenzoate are dissolved in about 38% by mass of distilled water at 60 to 65° C., the pH of the solution is adjusted by the addition of diluted aqueous sodium hydroxide solution to a value of 9 to 10, then the aqueous solution is admixed into the mixture of the lipophilic ingredients, and the emulsion obtained is stirred until cold. The active ingredient is dissolved in the remaining water, and the solution is admixed into the cooled cream.

EXAMPLE 2

Cream (Water/Oil)

| The cream consists of the following ingredients: | |
|---|---|
| compound „A" | 5.0% by mass |
| cetylstearyl alcohol | 12.0% by mass |
| white wax | 10.0% by mass |
| neutral oil | 35.0% by mass |
| Imwitor ® 780K (partial glycerides of vegetable fatty acids) | 5.0% by mass |
| methyl p-hydroxybenzoate | 0.1% by mass |
| distilled water | 32.9% by mass |
| | 100.0% by mass |

The ingredients are blended using the method described in Example 1.

EXAMPLE 3

Cream (Oil/Water)

| | |
|---|---|
| O-(3-piperidino-2-hydroxy-1-propyl)nicotinic amidoxime monohydrochloride | 15.0% by mass |
| glycerol | 6.8% by mass |
| stearic acid | 2.0% by mass |
| cetyl alcohol | 2.0% by mass |
| white petrolatum | 1.0% by mass |
| topical light mineral oil | 2.0% by mass |
| Ceteareth ® 6 [poly(ethylene glycol)cetostearyl ether] | 0.5% by mass |
| Ceteareth ® 25 [poly(ethylene glycol)cetostearyl ether] | 0.5% by mass |
| methyl p-hydroxybenzoate | 0.1% by mass |

-continued

| | |
|---|---|
| propyl p-hydroxybenzoate | 0.1% by mass |
| distilled water | 69.5% by mass |
| | 100.0% by mass |

The ingredients of the oil phase (stearic acid, cetyl alcohol, white petrolatum, topical light mineral oil, Ceteareth® 6 and Ceteareth® 25) are heated to 75° C. under stirring, thus, a melt of the oil phase is obtained. The glycerol, methyl and propyl p-hydroxybenzoate are dissolved in the distilled water while heating the solution to 75° C. In the clear solution obtained, the active ingredient is dissolved at the same temperature resulting in the aqueous phase. The oil phase is poured to the aqueous phase at 75° C. under constant stirring, then the mixture is homogenized under intensive stirring and allowed to cool under stirring. The cooled cream is filled into suitable containers.

EXAMPLE 4

Cream (Oil/Water)

| | |
|---|---|
| O-(3-piperidino-2-hydroxy-1-propyl)nicotinic amidoxime monohydrochloride | 20.0% by mass |
| glycerol | 6.8% by mass |
| stearic acid | 2.0% by mass |
| cetyl alcohol | 2.0% by mass |
| white petrolatum | 1.0% by mass |
| topical light mineral oil | 2.0% by mass |
| Ceteareth ® 6 [poly(ethylene glycol)cetostearyl ether] | 0.5% by mass |
| Ceteareth ® 25 [poly(ethylene glycol)cetostearyl ether] | 0.5% by mass |
| methyl p-hydroxybenzoate | 0.1% by mass |
| propyl p-hydroxybenzoate | 0.1% by mass |
| distilled water | 64.5% by mass |
| | 100.0% by mass |

The ingredients are blended using the method described in Example 3.

We claim:

1. A method for preventing actinic keratosis comprising applying to the affected skin surface an amount of a composition effective for preventing actinic keratosis, said composition comprising a hydroximic acid derivative of the formula $$R^3-A-\underset{\underset{NH_2}{|}}{C}=N-O-CH_2-\underset{\underset{OH}{|}}{CH}-CH_2-N\underset{R^2}{\overset{R^1}{<}} \quad I$$

wherein $R^1$ is a hydrogen atom or a $C_{1-5}$ alkyl group;

$R^2$ is a hydrogen atom or a $C_{1-5}$ alkyl group, a $C_{3-8}$ cycloalkyl group or a phenyl group, optionally substituted by a hydroxy group or a phenyl group; or $R^1$ and $R^2$ together with the nitrogen atom to which they are attached form a 5 to 8 membered saturated or unsaturated ring that optionally comprises one or more further nitrogen or oxygen atoms, wherein said ring can be optionally condensed with a benzene ring;

$R^3$ is a hydrogen atom, a phenyl group, a naphthyl group or a pyridyl group wherein said groups can optionally be substituted by one or more halo atoms or $C_{1-4}$ alkoxy groups;

A is a group of the formula $$-(CH)_m-\underset{\underset{R^4}{|}}{}-(CH)_n-\underset{\underset{R^5}{|}}{} \quad a$$

wherein $R^4$ is a hydrogen atom or a phenyl group;

$R^5$ is a hydrogen atom or a phenyl group;

m has a value of 0, 1 or 2; and n has a value of 0, 1 or 2;

or a physiologically acceptable acid addition salt thereof as the active ingredient.

2. The method of claim 1, wherein in the compound of the formula (I) $R^1$ and $R^2$ together with the nitrogen atom to which they are attached form a piperidino group, $R^3$ is a pyridyl or a phenyl group, A represents a group of the formula a, $$-(CH)_m-\underset{\underset{R^4}{|}}{}-(CH)_n-\underset{\underset{R^5}{|}}{} \quad a$$

wherein $R^4$ is a hydrogen atom or a phenyl group;

$R^5$ is a hydrogen atom or a phenyl group;

and m and n have a value of 0.

3. The method of claim 1, wherein the compound of the formula (I) is O-(3-piperidino-2-hydroxy-1-propyl)nicotinic amidoxime or an acid salt thereof.

4. The method of claim 1, wherein the active ingredient is present at 0.1 to 30% by mass of the composition.

5. The method of claim 1, wherein the active ingredient is present at 5 to 15% by mass of the composition.

6. The method of claim 2, wherein the active ingredient is present at 5 to 15% by mass of the composition.

7. The method of claim 3, wherein the active ingredient is present at 5 to 15% by mass of the composition.

* * * * *